United States Patent [19]
Yano et al.

[11] Patent Number: 5,295,083
[45] Date of Patent: Mar. 15, 1994

[54] DEVICE FOR DYNAMICALLY MEASURING BUBBLE CONTENT OF FLOWING LIQUID

[75] Inventors: Hisashi Yano; Mitulu Fujioka, both of Kanagawa; Koji Tsuchimoto, Chiba; Junsuke Yabumoto, Kanagawa, all of Japan

[73] Assignee: Mitsubishi Oil Co., Ltd., Tokyo, Japan

[21] Appl. No.: 787,606

[22] Filed: Nov. 4, 1991

[30] Foreign Application Priority Data

Nov. 5, 1990 [JP] Japan .................................. 2-297151

[51] Int. Cl.$^5$ .............................................. G01N 29/00
[52] U.S. Cl. .................................... 364/510; 364/558; 73/19.04; 73/19.05
[58] Field of Search ........................ 364/509, 510, 558; 73/19.04, 19.05, 23.28, 23.29

[56] References Cited

U.S. PATENT DOCUMENTS

| | | | |
|---|---|---|---|
| 4,763,525 | 8/1988 | Cobb | 73/599 |
| 4,862,729 | 9/1989 | Toda et al. | 73/19.05 |
| 5,041,990 | 8/1991 | Yabumoto et al. | 364/510 |

FOREIGN PATENT DOCUMENTS 0380759  8/1990  European Pat. Off. .
8912802  8/1991  European Pat. Off. .

*Primary Examiner*—Thomas G. Black
*Assistant Examiner*—Michael Zanelli
*Attorney, Agent, or Firm*—Sughrue, Mion, Zinn, Macpeak & Seas

[57] ABSTRACT

A device for dynamically measuring the bubble content of a flowing liquid is arranged in a conveyance passage for a flowing liquid or provided in a simple bypass for the conveyance passage of the liquid so that the bubble content of the flowing liquid and the bubble quantity of dissolved gas in the flowing liquid can be dynamically measured due to a change in the pressure of the liquid in the passage or the bypass without extracting any of the liquid therefrom.

4 Claims, 5 Drawing Sheets

DEVICE FOR DYNAMICALLY MEASURING BUBBLE CONTENT OF FLOWING LIQUID

BACKGROUND OF THE INVENTION

The present invention relates to a device for dynamically measuring the bubble content of a flowing liquid. More particularly, the invention relates to a device provided in a conveyance passage for a flowing liquid, as may be used in the chemical or mechanical industries, or provided in a simple bypass for the conveyance passage, so that the bubble content of the flowing liquid and the bubble quantity of dissolved gas in the flowing liquid can be dynamically measured without extracting any of the liquid therefrom.

When a liquid such as a lubricating oil and a liquid containing a polymer, a surface active agent or the like flows through a passage with agitation, bubbles are likely to be produced in the liquid. The bubbles contained in the liquid are likely to cause various problems, such as an inaccurate measurement of the flow rate of the liquid, or, in the case that the liquid is a lubricating oil, a drop in the efficiency of operation of a hydraulic apparatus operated by the liquid and abnormal wear of the lubricated sliding surfaces of the machine. Although it is often necessary to dynamically, quickly and accurately measure the bubble content of a liquid, no appropriate measuring device has heretofore been available. Conventionally, a sample of the liquid has been extracted from a passage for the liquid and subjected to a gas chromatography or a static separation process. However, such procedures are time consuming, the bubbles in the liquid are likely to disappear, and it is difficult to accurately measure the bubble content of the liquid.

Accordingly, to overcome the above problems, a method and a device for dynamically measuring the bubble content of a flowing liquid without extracting any of the liquid from a passage were disclosed in U.S. Pat. No. 5,041,990. The device is installed in a conveyance passage of a bubble-containing liquid or in a bypass of the passage. The device includes a density sensor sensitive to the density of the bubble-containing liquid, a pressure sensor, a temperature sensor, a pressure calculation circuit, a temperature calculation circuit, a bubble content calculation circuit, a control panel, and a bubble content display panel. The density of the liquid, which changes depending on the bubble content of the liquid, is first measured. The pressure calculation circuit, the temperature calculation circuit, and the bubble content calculation circuit then carry out calculations in accordance with a predetermined formula and an instruction from the control panel to determine the bubble content of the flowing liquid at a standard pressure and a standard temperature. The bubble content determined in this manner is indicated on the bubble content display panel.

Although the bubble content of the liquid at high pressure can be measured by the method and device disclosed in the above-mentioned patent, there is still such a problem that it is difficult for the method and the device to dynamically measure the bubble content of the liquid at low pressure and the quantity of dissolved gas in the liquid.

SUMMARY OF THE INVENTION

Accordingly, it is an object of the present invention to overcome the problems described above regarding measurements. It is a specific object of the invention to provide a device which includes a mass flow meter, a volumetric flowmeter and passage changeover valves, in addition to the prior art disclosed in U.S. Pat. No. 5,041,990, and which operates in accordance with improved calculation formulae so that the bubble content of a flowing liquid can be measured accurately at either high pressure or low pressure, and the bubble quantity of dissolved gas in the flowing liquid without extracting the liquid.

If the device of the present invention is an integrated type, the device is installed in a conveyance passage in which the bubble-containing liquid flows. The device includes pressure regulation valves for regulating the pressure of the bubble containing liquid, a mass flowmeter for measuring the mass flow rate of the liquid, a volumetric flowmeter for measuring the volumetric flow rate of the liquid, a pressure sensor for measuring the pressure of the liquid, a temperature sensor for measuring the temperature of the liquid, and passage changeover valves for altering the order of flow of the liquid through the mass flowmeter and the volumetric flowmeter.

If the device is of a separate "stand-alone" type, it is installed in a bypass of the conveyance passage. In this case, the pressure regulation valves, the mass flowmeter, the volumetric flowmeter, the pressure sensor and the temperature sensor are connected to the bypass which connects to the conveyance passage with pipe joints to introduce the liquid into the bypass, and a pump having a function of circulating the liquid in the pump is installed in the bypass.

In either case, the device further includes a pressure calculation circuit, a temperature calculation circuit, a bubble content calculation circuit, a control panel, a bubble content display panel, a pressure display panel and a temperature display panel.

The mass flow rate, volumetric flow rate, pressure and temperature of the bubble-containing liquid flowing in the conveyance passage or the bypass are measured and subjected to calculations in the pressure calculation circuit, the temperature calculation circuit and the bubble content calculation circuit in accordance with formulae (1), (2) and (3) given below, so that the bubble content of the flowing liquid at either high pressure or low pressure and the bubble quality of disolved gas in the flowing liquid due to a change in pressure of the liquid can be dynamically, quickly and accurately determined in terms of a standard pressure (such as an absolute pressure of 1.03 kg/cm$^2$) and a standard temperature (such as 15° C.).

$$X_{ho} = \frac{V_{hao}}{V_{hlo} + V_{hao}} \times 100 \quad (1)$$

$$X_{lo} = \frac{V_{lao}}{V_{llo} + V_{lao}} \times 100 \quad (2)$$

$$X_{so} = X_{lo} - X_{ho} \quad (3)$$

In the formulae, $V_{hao}$, $V_{lao}$, $V_{hlo}$, $V_{llo}$, $X_{ho}$, $X_{lo}$ and $X_{so}$ respectively denote the volume of the bubbles contained in the liquid at the standard pressure and the standard temperature for high pressure, the volume of the bubble in the liquid at the standard pressure and the standard temperature for low pressure, the volume of the liquid at the standard pressure and the standard temperature for high pressure, the volume of the liquid at the standard pressure and the standard temperature for low pressure, the bubble content (% by volume) of the liquid at the standard pressure and the standard temperature for high pressure, the bubble content (% by volume) of the liquid at the standard pressure and the standard temperature for low pressure, and the bubble quantity (% by volume) of the dissolved gas in the liquid at the time of a change in the pressure of the liquid from high pressure to low pressure at the standard pressure and the standard temperature.

The gas bubble content can be calculated in accordance with the following formula:

$$X_0 = \frac{\frac{\rho_l - \rho_m}{\rho_l - \rho_a} \cdot \frac{273 + t}{273 + t_0} \cdot \frac{P}{P_0} \cdot 100}{\left(1 - \frac{\rho_l - \rho_m}{\rho_l - \rho_a}\right) \cdot \frac{VCF(t)}{VCF(t_0)} + \frac{\rho_l - \rho_m}{\rho_l - \rho_a} \cdot \frac{273 + t_0}{273 + t} \cdot \frac{P}{P_0}} \quad (4)$$

wherein:

$X_o$ 32 gas bubble content by volume percentage in the fluid at $t_o$ °C. and $P_o$ kg/cm² abs.

$\rho_l$ = density of gas-free liquid in g/cm³ at t °C. and P kg/cm² abs.

$\rho_a$ = gas density in g/cm³ at t°C. and P kg/cm² abs.

$\rho_m$ = average density of the fluid in g/cm³ at t°C. and P kg/cm² abs calculated in accordance with a volumetric flow rate (Vf) and a mass flow rate (Wf) of the fluid ($\rho_m$ = Wf/Vf).

$t_o$ = normalized temperature in °C.

t = fluid temperature in °C.

$P_o$ = normalized pressure in kg/cm² abs.

P = fluid pressure in kg/cm² abs.

VCF($t_o$) = volume correction factor of gas-free liquid at a temperature of $t_o$ °C., VCF($t_o$) = $\rho_{l.0}/\rho_{l.15}$, where $\rho_{l.15}$ and $\rho_{l.0}$ are the density of gas-free liquid at a temperature of 15° C. and $t_0$ °C., respectively.

VCF(t) = volume correction factor of gas-free liquid of a temperature of t°C. VCF(t) = $\rho_l/\rho_{l.15}$, where $\rho_{l.15}$ and $\rho_l$ are the density of gas-free liquid at a temperature of 15° C. and t °C., respectively.

In the above formula (4) the demoninator $$\left(1 - \frac{\rho_l - \rho_m}{\rho_l - \rho_a}\right) \cdot \frac{VCF(t)}{VCF(t_0)} + \frac{\rho_l - \rho_m}{\rho_l - \rho_a} \cdot \frac{273 + t_0}{273 + t} \cdot \frac{P}{P_0}$$

corresponds to $V_{hlo} + V_{hao}$ and $V_{llo} + V_{lao}$, respectively, and the numerator $$\frac{\rho_l - \rho_m}{\rho_l - \rho_a} \cdot \frac{273 + t}{273 + t_0} \cdot \frac{P}{P_0}$$

corresponds to $V_{hao}$ and $V_{lao}$, respectively.

FIG. 5 is a diagram indicating schematically the obtention of the various parameters and the calculations carried out by the data processor.

In the device provided in accordance with the present invention, data necessary for the calculation of the bubble content of the flowing liquid are entered through the control panel. The bubble-containing liquid is then caused to flow through the conveyance passage or the bypass. If the liquid is caused to flow through the conveyance passage, the mass flow rate, volumetric flow rate, pressure and temperature of the liquid are measured and the calculations are thereafter made by the pressure calculation circuit, the temperature calculation circuit and the bubble content calculation circuit. If the liquid is caused to flow through the bypass, the liquid is introduced into the bypass by the pump having a circulating function for pulverizing the bubble in the liquid to uniformly disperse the pulverized elements of the bubble, the mass flow rate, volumetric flow rate, pressure and temperature of the liquid are then measured, and the calculations are thereafter made by the above-mentioned circuits. The bubble content of the liquid flowing in the conveyance passage or the bypass passage can then be dynamically, quickly and accurately determined in terms of the standard pressure and the standard temperature, and then displayed to the operator on the bubble content display panel.

When the bubble content of the flowing liquid at high pressure and that of the liquid at low pressure are to be alternately measured by the device through shifting the passage changeover valves, the liquid is caused to flow through the conveyance passage or the bypass and set at the high pressure or the low pressure by the pressure regulation valves, and the order of flow of the liquid through the mass flowmeter and that of the liquid through the volumetric flowmeter is then altered by shifting the passage changeover valves, so that the mass flow rate, volumetric flow rate, pressure and temperature of the liquid are measured at high pressure or at low pressure. The measured quantities are subjected to the calculations by the pressure calculation circuit, the temperature calculation circuit and the bubble content calculation circuit so that the bubble content of the liquid at high pressure and of low pressure is determined in terms of the standard pressure and the standard temperature, and displayed on the bubble content display panel. The bubble content of the flowing liquid at high pressure and at low pressure can thus be alternately measured, and then indicated on the panel.

When the bubble content of the flowing liquid at the high pressure set by the pressure regulation valves and that of the flowing liquid at the flow pressure set by the valves are to be simultaneously measured by the device, the bubble-containing liquid is caused to flow through the conveyance passage or the bypass, the volumetric flow rate, pressure and temperature of the liquid set at the high pressure are measured, the mass flow rate of the liquid is then measured, and the volumetric flow rate, pressure and temperature of the liquid set at the low pressure by the downstream pressure regulation valve are thereafter measured. The measured quantities are subjected to calculations by the pressure calculation circuits, the temperature calculation circuits and the bubble content calculation circuits for high pressure and for low pressure so that the bubble content of the liquid at high pressure and low pressure are determined in terms of the standard pressure and the standard temperature in accordance with calculation formulae (1) and (2), and then indicated on the respective bubble content display panels.

In accordance with calculation formula (3), the difference between the bubble content of the liquid at low pressure and that of the liquid at high pressure can be determined as the bubble quantity of the dissolved gas bubbled in the liquid due to the change in the pressure thereof.

DESCRIPTION OF THE PREFERRED EMBODIMENTS

Two preferred embodiments of the present invention are hereafter described. However, the invention is not confined to these embodiments.

Embodiment 1

Figure 1:
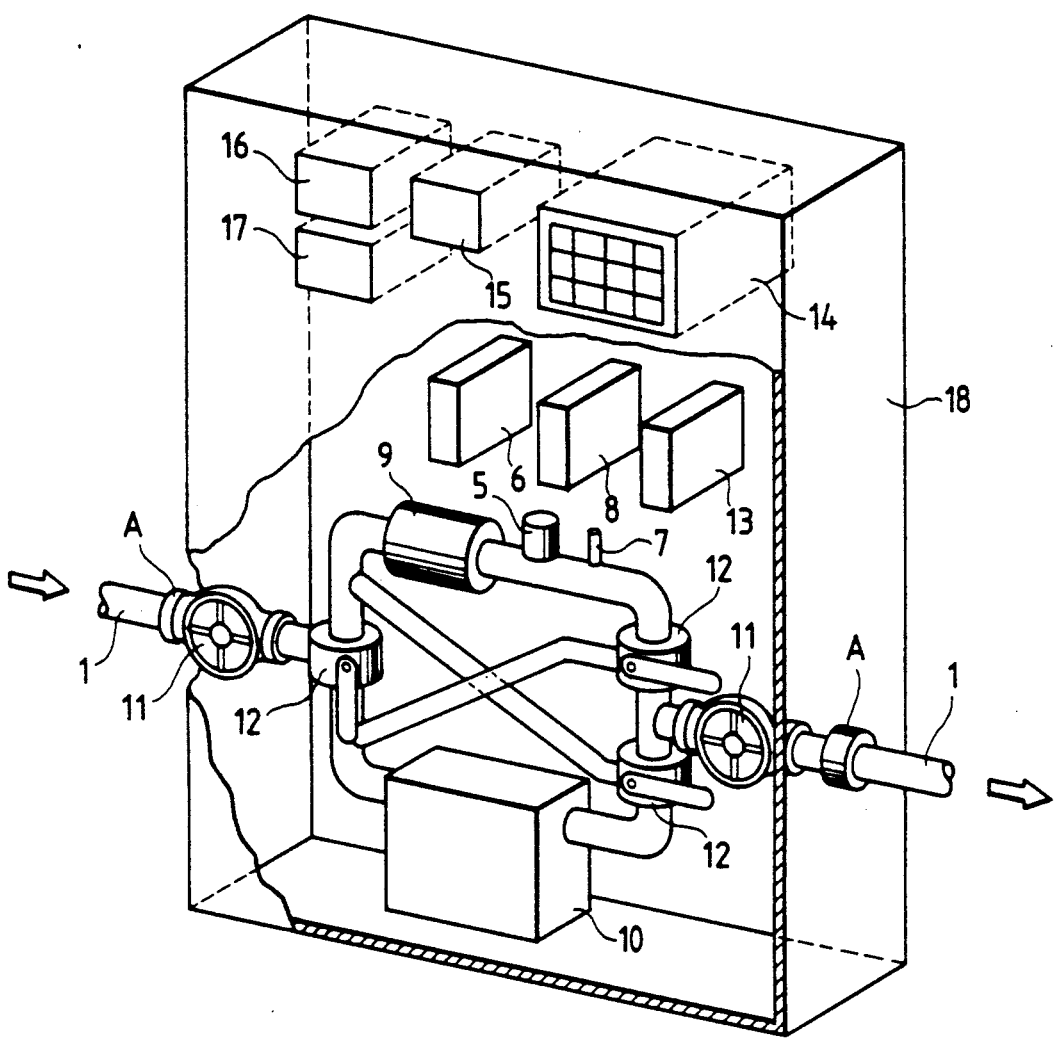
FIG. 1 is a cutaway view of an integrated-type device of the invention for dynamically measuring the bubble content of a flowing liquid, which is directly installed in a conveyance passage for the liquid.
Figure 2:
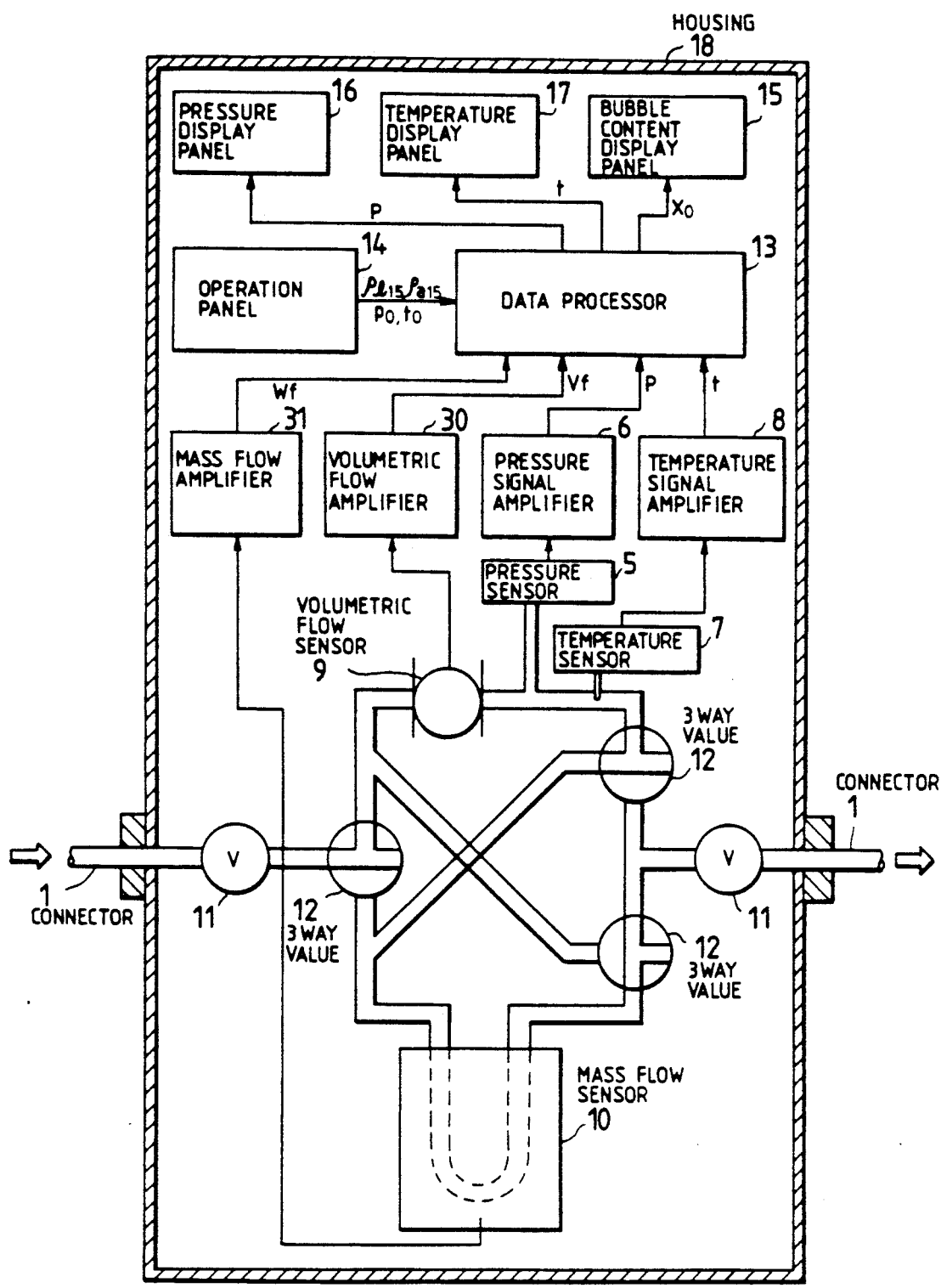
FIG. 2 is a block diagram of the device of FIG. 1.

One of the two preferred embodiments is an integrated-type device intended for dynamically measuring the bubble content of a flowing liquid and which is installed in the mixed oil conveyance passage of a mixer for mixing a lubricating oil with a polymer. The device includes a pressure sensor 5, a pressure calculation circuit 6, a temperature sensor 7, a temperature calculation circuit 8, a volumetric flowmeter 9, a volumetric flow amplifier 30, a mass flowmeter 10, a mass flow amplifier 31, pressure regulation valves 11, passage changeover valves 12, a bubble content calculation circuit 13 which operates in accordance with bubble content calculation formulae (1) and (2) above, a control panel 14, a bubble content display panel 15, a pressure display panel 16 and a temperature display panel 17, as shown in FIGS. 1 and 2. These components are provided in housing box 18. The pressure sensor 5, the temperature sensor 7, the volumetric flowmeter 9, the mass flowmeter 10, the pressure regulation valves 11 and the passage changeover valves 12 are connected to each other by pipes as shown. The housing 18 is provided in the conveyance passage 1 of the mixer in such a manner that the pipes of the device are connected to the passage by pipe joints A. The sensors 5 and 7, the flowmeters 9 and 10, the flow amplifier 30 and 31, the calculation circuits 6, 8 and 13, and the panels 14, 15, 16 and 17 are electrically coupled together by wires. The control panel 14 can be manipulated in front of the device. The values shown on the bubble content display panel 15, the pressure display panel 16 and the temperature display panel 17 can be seen in front of the device.

Embodiment 2

Figure 3:
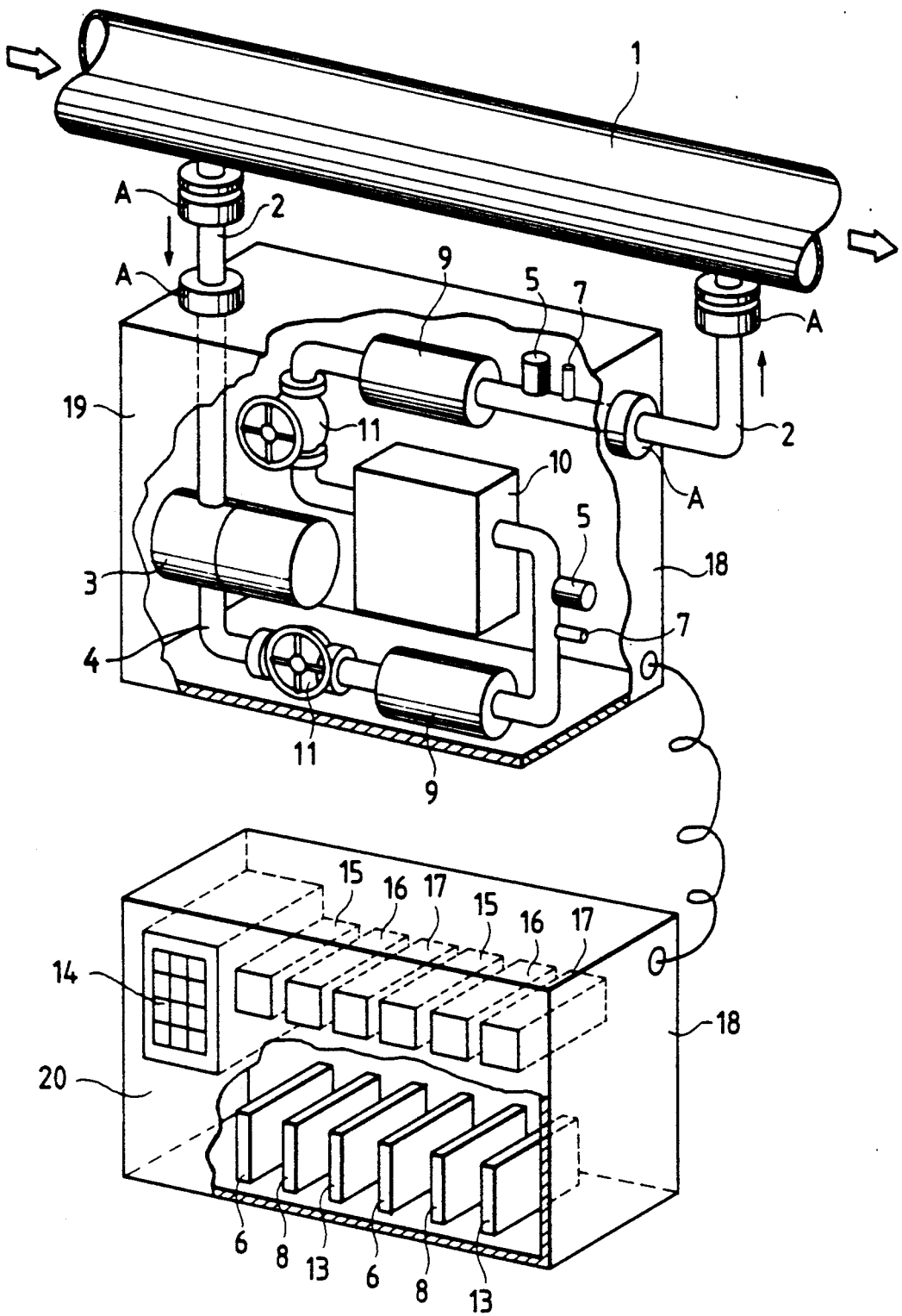
FIG. 3 is a cutaway view of a separate type device for dynamically measuring the bubble content of a flowing liquid, which is installed in a bypass for the liquid.
Figure 4:
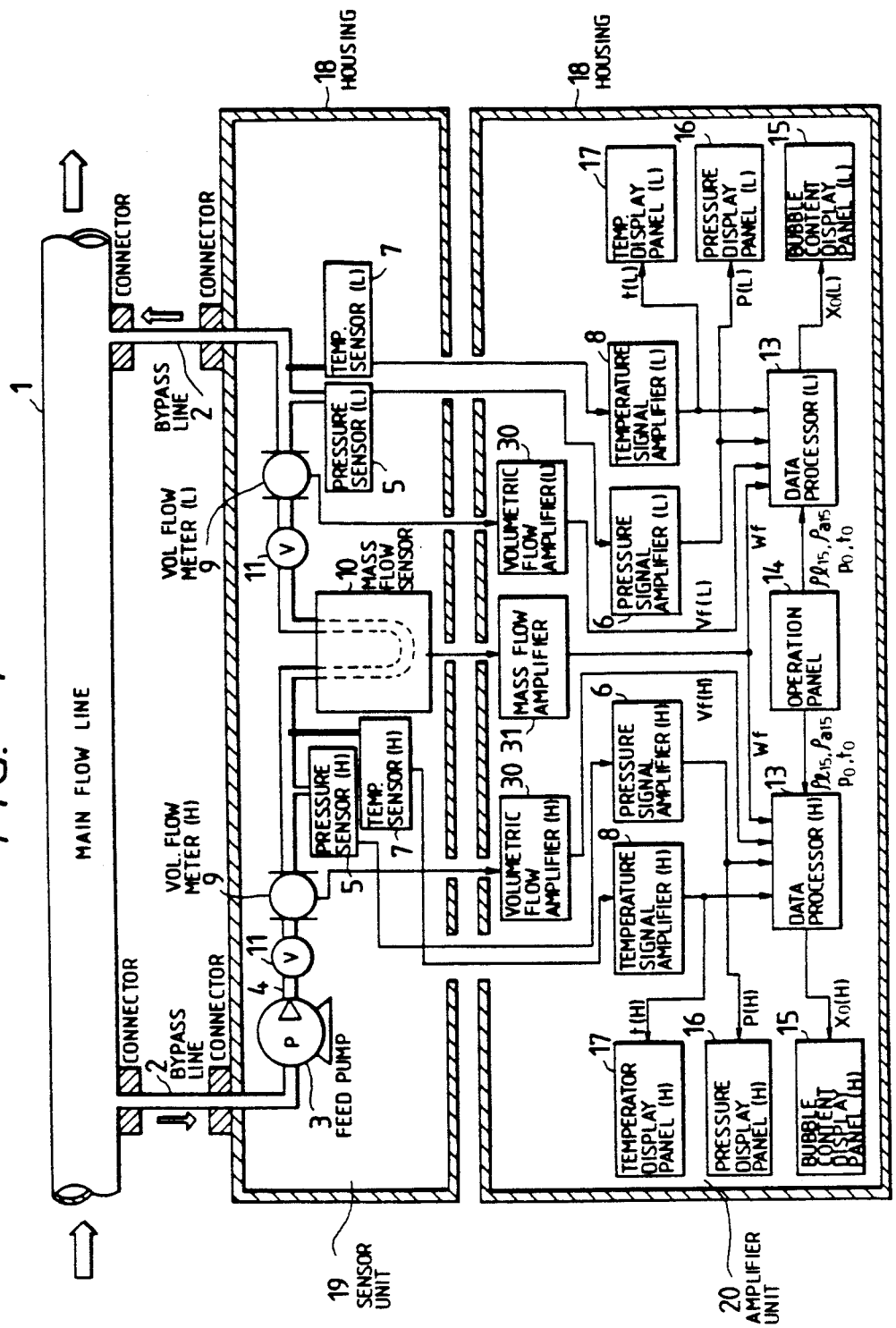
FIG. 4 is a block diagram of the separate type device.
Figure 5:
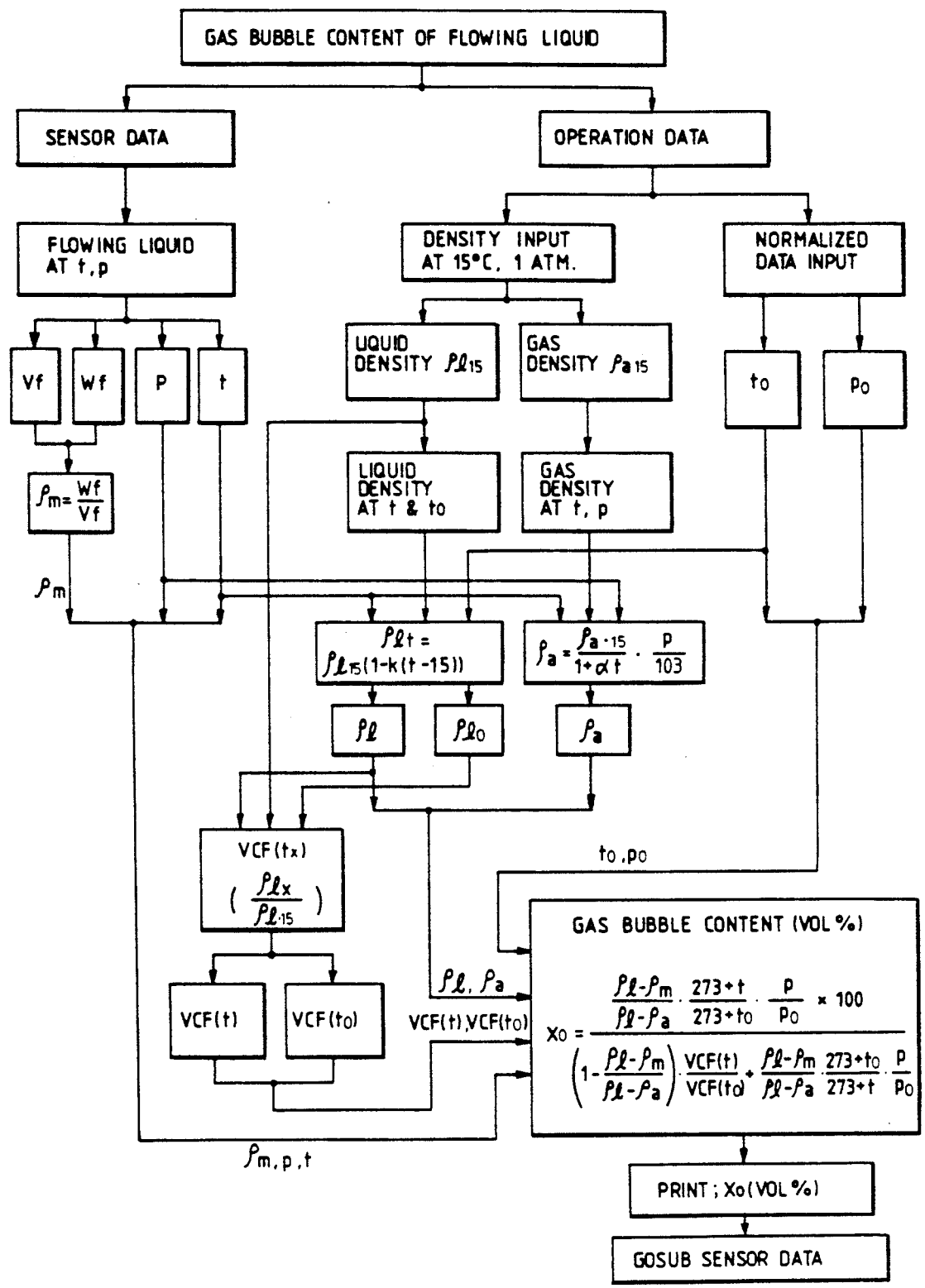
FIG. 5 is a diagram showing the operation of a data processor used in the above embodiments.

The second embodiment is a separate type device intended for dynamically measuring the bubble content of a flowing liquid and which is installed in a bypass of the lubricating oil conveyance passage of a 2,000 cc four-cycle engine for a motor vehicle. The device includes a pump 3 having a function of circulating the liquid in the pump, a connection pipe 4, a high-pressure section including a pressure sensor 5, a pressure calculation circuit 6, a temperature sensor 7, a temperature calculation circuit 8, a volumetric flowmeter 9, a volumetric flow amplifier 30, a pressure regulation valve 11, a bubble content calculation circuit 13 operating in accordance with calculation formula (1) above, a bubble content display panel 15, a pressure display panel 16 and a temperature display panel 17, a low-pressure section including a pressure sensor 5, a pressure calculation circuit 6, a temperature sensor 7, a temperature calculation circuit 8, a volumetric flowmeter 9, a volumetric flow amplifier 30, a pressure regulation valve 11, a bubble content calculation circuit 13 operating in accordance with calculation formula (2), a bubble content display panel 15, a pressure display panel 16 and a temperature display panel 17, a mass flowmeter 10, a mass flow amplifier 31, and a control panel 14, as shown in FIGS. 3 and 4. These components are provided in housing boxes 18. Two tapped holes are provided in the lubricating oil conveyance passage 1 of the engine. The bypass 2 is connected to the passage by pipe joints A screw-engaged in the tapped holes. The sensors, the calculation circuits, the flowmeters, the flow amplifiers and the panels are electrically coupled together by wires so that the device is composed of a bubble content measuring detector 19 connected to the bypass 2, and a bubble content measuring data processor 20 electrically coupled to the detector.

With the device of the present invention, a flowing liquid containing bubbles does not need to be extracted from a passage for the liquid for measuring the bubble content of the liquid. For this reason, the bubble content can be measured as the liquid remains flowing in the passage. Moreover, the bubbles do not disappear by the measurement. Since pressure regulation valves, a volumetric flowmeter, a mass flowmeter and so forth are provided and novel calculation formulae are employed, the bubble content can be dynamically, quickly and accurately measured not only at high pressure, as in the conventional case, but also at low pressure, and the bubble quantity of the dissolved gas in the liquid due to a change in the pressure thereof can be dynamically, quickly and accurately measured.

The bubble content measuring detector of a separate type device such as the second embodiment can be used in a severe environment of high or low temperature, while the bubble content measuring data processor of the device can be used in a normal environment. For this reason, the range of use of the device is wide. Since a pump having a function of circulating the liquid is provided to pulverize the bubbles in the liquid at the time of introduction of the liquid into the device to uniformly disperse the pulverized elements of the bubbles, the dispersion in the measured value of the bubble content of the liquid is reduced. Although it is difficult to obtain accurate data as to the bubble content of a flowing liquid in a conventional device, the bubble content can be continuously measured under various conditions in accordance with the present invention to make it easier to control the quality of each of various kinds of liquids.

The present invention can be utilized for research as well as for practical use. Since the maximum rotational speeds of automobile and motorcycle engines have recently been increased, the bubble content of the lubricating oil for the engine has become very large. The bubbles are likely to do various kinds of harm to the hydraulic mechanism and sliding surfaces of the engine. However, since there has not been a method for quickly and accurately measuring the bubble content of the lubricating oil under various conditions during the actual flow of the oil, it was difficult to fully clarify the quantitative relationship between the bubble content and the degree and type of the damage. The present invention can be applied for such full clarification in research.

What is claimed is:

1. A device for dynamically measuring a bubble content of a flowing liquid and a bubble quantity of the dissolved gas in said liquid during the flowing thereof, comprising:

means for measuring a pressure, a temperature and volumetric flow rate of a liquid in a conveyance passage or a bypass passage for said conveyance passage for said liquid at high and low pressure points and a mass flow rate of said liquid between said high and low pressure points; and means for calculating the bubble content and the bubble quantity of the dissolved gas in said liquid in accordance with the measured values of said pressures, said temperatures, said volumetric flow rate and said mass flow rate.

2. The device of claim 1, further comprising a passage changeover valve means for switching a flow of said liquid to determine said high and low pressure points.

3. The device of claim 1, where said calculating means calculate said bubble content in accordance with the following formula:

$$X_0 = \frac{\frac{\rho_l - \rho_m}{\rho_l - \rho_a} \cdot \frac{273 + t}{273 + t_0} \cdot \frac{P}{P_0} \cdot 100}{\left(1 - \frac{\rho_l - \rho_m}{\rho_l - \rho_a}\right) \cdot \frac{VCF(t)}{VCF(t_0)} + \frac{\rho_l - \rho_m}{\rho_l - \rho_a} \cdot \frac{273 + t_0}{273 + t} \cdot \frac{P}{P_0}}$$

wherein:

$X_o$ = gas bubble content by volume percentage in the liquid at $t_o$ °C. and $P_o$ kg/cm² abs, $\rho_l$ = density of gas-free liquid in g/cm³ at t °C. and P kg/cm² abs, $\rho_a$ = gas density in g/cm³ at t°C. and P kg/cm² abs, $\rho_m$ = average density of the liquid in g/cm³ at t°C. and P kg/cm² abs calculated in accordance with a volumetric flow rate (Vf) and the mass flow rate (Wf) of the liquid ($\rho_m$ = Wf/Vf)

$t_o$ = normalized temperature in °C.

t = liquid temperature in °C.

$P_o$ = normalized pressure in kg/cm² abs.

P = liquid pressure in kg/cm² abs.

VCF($t_o$) = volume correction factor of gas-free liquid at a temperature of $t_o$ °C. VCF($t_o$) = $\rho_{l,0}/\rho_{l,15}$, where $\rho_{l,15}$ and $\rho_{l,0}$ are the density of gas-free liquid at a temperature of 15° C. and t°C., respectively.

VCF(t) = volume correction factor of gas-free liquid at a temperature of t°C. VCF(t) = $\rho_l/\rho_{l,15}$, where $\rho_{l,15}$ and $\rho_l$ are the density of gas-free liquid at a temperature of 15° C. and t°C., respectively.

4. A device as claimed in claim 1 wherein said means for measuring comprises a regulation valve for regulating a pressure of said liquid.

* * * * *